United States Patent
Tong et al.

(10) Patent No.: US 6,251,941 B1
(45) Date of Patent: Jun. 26, 2001

(54) USE OF INHALED RETINOIDS IN THE PREVENTION OF CANCER

(75) Inventors: William P. Tong, Flushing, NY (US); Raymond P. Warrell, Westfield, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/171,478

(22) PCT Filed: Apr. 21, 1997

(86) PCT No.: PCT/US97/05409

§ 371 Date: Dec. 29, 1998

§ 102(e) Date: Dec. 29, 1998

(87) PCT Pub. No.: WO97/39745

PCT Pub. Date: Oct. 30, 1997

Related U.S. Application Data

(60) Provisional application No. 60/016,246, filed on Apr. 19, 1996.

(51) Int. Cl.$^7$ .............................. A01N 37/00; A61K 31/20
(52) U.S. Cl. ............................................... 514/559; 424/45
(58) Field of Search ................................ 514/559; 424/45

(56) References Cited

U.S. PATENT DOCUMENTS 4,529,600    7/1985    Dawson et al. ....................... 514/529

OTHER PUBLICATIONS

Hong et al., "Prevention of Secon Primary Tumors with isotretinon in squammous–cell carcinoma of the head and neck", New Engl. J. Med. 323:795–801, (1990).*

Moren et al., Aerosols in Medicine, Principles, Diagnosis and Therapy, 1993.*

*Aerosols in Medicine,* F. Moren et al., eds. Elsevier, New York, New York, 1993.

Molecusol brochure (1988).

Hong et al., "Prevnetion of Second Primary Tumors with Isoretinoin in Squamous–Cell Carcinoma of the Head and neck" *New Engl. J. Med.* 323: 795–801 (1990).

Laznitzki et al., "Prevention and Reversal by a Retinoid of 3,4–beanzpyrine—and Cigarette Smoke Condensate–induced Hyperplasia and Metaplasia of Rodent Respiratory Epithelia in Organ Culture", *Cancer Treatment Rep.* 66: 1375–1380 (1982).

Warrell, Jr., R.P., "Retinoids in Cancer", in *ImmunoPharmaceuticals,* E.S. Kimball, ed., CRC Press, New York, New York, 1993, pp. 101–128.

Osol et al.., Editor of Remington's Pharmaceutical Sciences, 15th Edition, 1975, p. 1651.*

Windholz et al., Editor of The Merk Index, 10th Edition, p. 1381, 1983.*

Stein et al., Editor of Internal Medicine, 45th Edition, Chapters 71–72, pp. 699–715, 1993, 1975.*

* cited by examiner

*Primary Examiner*—Dwayne C. Jones
(74) *Attorney, Agent, or Firm*—Oppedahl & Larson LLP

(57) ABSTRACT

Administration of retinoids by inhalation is used to overcome the chronic toxicity problems presented by systemic administration and to make retinoid therapy available as an option for the prevention of epithelial cancers of the respiratory tract, especially those that are associated with tobacco use. Retinoids are administered by inhalation to the respiratory tract of the individual as an air-borne composition with a metered dose aerosol-producing inhaler, in which the retinoid is dissolved in a combination of a pharmaceutically acceptable chlorofluorocarbon propellant and an alkylamine solubilizing agent.

22 Claims, 3 Drawing Sheets

ALL-TRANS RETINOL

14-HYDROXY-RETRO-RETINOL

ALL-TRANS RETINOIC ACID

N-(4-HYDROXYPHENYL) RETINAMIDE

13-CIS RETINOIC ACID

3-METHYL TTNEB

9-CIS RETINOIC ACID

MEAN PLASMA LEVELS OF ATRA
(n=3-5 TIME POINT [TP]), IV (n=5/TP), OR INTRA-TRACHEAL
INJECTION (n=3/TP).

MEAN LIVER LEVELS OF ATRA
(n=3-5/TIME POINT[TP]), IV (n=5/TP), OR INTRA-TRACHEAL
INJECTION (n=3/TP).

LOG OF MEAN LUNG LEVEL OF ATRA
(n=3-5/TIME POINT [TP]), IV (n=5/TP), OR INTRA-TRACHEAL
INJECTION (n=3/TP). THERE IS NO DATA FOR THE INTRA-
TRACHEAL OR IV DOSED ANIMALS AT 24 HRS.

USE OF INHALED RETINOIDS IN THE PREVENTION OF CANCER

This application is a national phase of International Application Ser. No. PCT/US97/05409 filed Apr. 21, 1997 which claims priority from U.S. Provisional Application Ser. No. 60/016,246 filed Apr. 19, 1996.

BACKGROUND OF THE INVENTION

Retinoids are a class of naturally occurring and synthetic derivatives of Vitamin A which function in vivo as regulators of a number of physiological functions including cellular proliferation, cytodifferentiation and embryonal morphogenesis. This class includes a number of clinically important compounds such as those shown FIG. 1 which have been shown or hypothesized to have utility in the therapy and prevention of various types of cancer. For example, Hong et al., N. Eng. J. Med. 323: 795–801 (1990) have shown that adjuvant treatment with 13-cis retinoic acid after definitive anti-cancer treatment in patients with carcinoma of the head and neck significantly reduces the incidence of secondary tumors of the aerodigestive tract. Head and neck cancer, like lung cancer, is significantly related to tobacco smoking, and in fact many of the tumors reduced in incidence in the Hong et al. study were lung cancers. Retinoids have also been shown to be effective in the prevention and reversal of certain types of induced hyperplasia and metaplasia in cultured rodent respiratory epithelia. Lasnitzki et al., Cancer Treatment Reports 66: 1375–1380 (1982).

Unfortunately, while retinoids have been shown to provide beneficial effects in the prevention of at least some types of cancer, the therapeutic regiment requires chronic administration. Under these circumstances, substantial systemic toxicity may result, including hyperlipidemia, hypercalcemia, and skin, liver and central nervous system toxicity. This toxicity has limited the utility of retinoids as therapeutic agents in the prevention of cancer.

SUMMARY OF THE INVENTION

We have now developed a system for administration of retinoids by inhalation to overcome the chronic toxicity problems presented by systemic administration and to make retinoid therapy available as an option for the prevention of epithelial cancers of the respiratory tract, especially those that are associated with tobacco use. Thus, in accordance with the present invention, there is provided a method for prevention of epithelial cancer of the respiratory tract in an at-risk individual, comprising administering by inhalation to the respiratory tract of the individual an air-borne composition (i.e., an aerosol or finely divided dry powder) comprising a therapeutically effective amount of at least one retinoid. The retinoid is suitably administered with a metered dose aerosol producing inhaler, in which the retinoid is dissolved in a combination of a pharmaceutically acceptable chlorofluorocarbon propellant and an amine solubilizing agent.

DETAILED DESCRIPTION OF THE INVENTION

Figure 1:
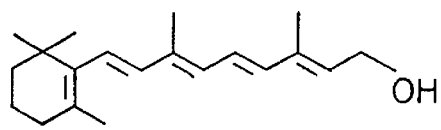
FIG. 1 shows the structures of various clinically significant retinoids.
Figure 1:
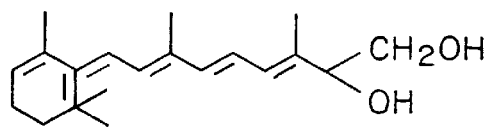
Figure 1:
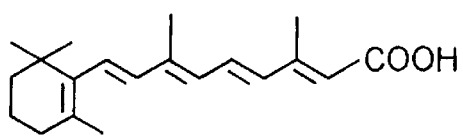
Figure 1:
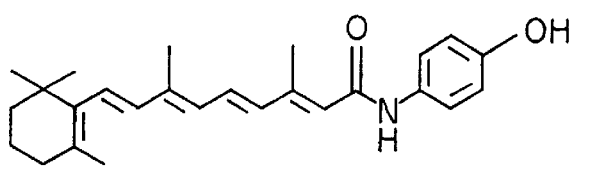
Figure 1:
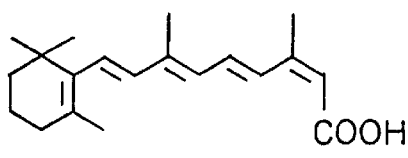
Figure 1:
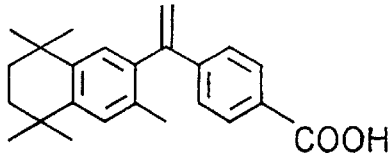
Figure 1:
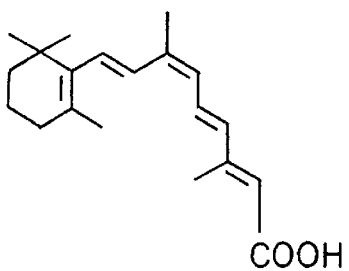
Figure 2:
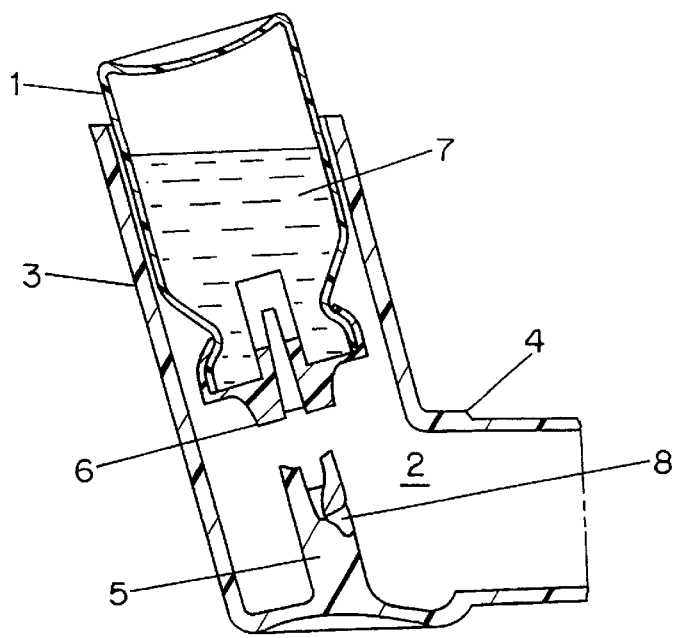
FIG. 2 shows an inhaler in accordance with the invention.

The present invention relates to the prevention of epithelial cancer of the respiratory tract in an at-risk individual by administering by inhalation to the respiratory tract of the individual an aerosol comprising a therapeutically effective amount of at least one retinoid. The method provides delivery of the pharmaceutically active retinoid directly to the affected areas, thus increasing bioavailability and decreasing systemic toxicity. It will be recognized by persons skilled in the art that "prevention" of cancer is difficult to prove in the absolute sense because one cannot predict with certitude what will transpire in the future. Thus, as used in the specification and claims of this application, the terms "prevention" or "preventing" refer to a reduction of the risk of contracting epithelial cancer, or to a delay in the onset of epithelial cancer.

Inhalation of pharmaceutically-active compositions is not a new concept, and various compounds used in asthma therapy and the like have been administered in this manner. Commonly, however, such aerosols are formed from the active compounds solubilized in water. However, most retinoids of clinical interest, including all of the "natural retinoids" such as all-trans retinoic acid, 13-cis retinoic acid and 9-cis retinoic acid, are highly lipophilic and thus very insoluble in water. For this reason, conventional water-based formulations cannot be used for aerosol administration of these compounds. To make it possible to perform inhalation therapy using retinoids, it was therefore necessary to define a solvent system which (1) solubilized sufficient amounts of the retinoids to provide a pharmaceutically-useful dosage, i.e. from about 0.1 to 5.0 mg/ml; (2) provided a retinoid solution of sufficient stability to permit distribution of a product; and (3) was substantially non-toxic in the amounts administered and thus suitable for administration to living patients.

Working towards this goal, we first looked at organic solvents. In the course of this investigation, we found that retinoids were only slightly soluble in ethanol or ethyl acetate. Methylene chloride or chloroform provided adequate solubilization, but the potential toxicity of these materials argued against their use as carriers in an aerosol for use in inhalation therapy.

Next, because of a report that the solubility of retinol (vitamin A) in water could be increased by addition of modified beta cyclodextrin (MOLECUSOL®), we next tried to prepare aqueous solutions of all-trans retinoic acid using MOLECUSOL® to enhance the solubility. Solutions containing 45% MOLECUSOL® did in fact enhance the solubility of the all-trans retinoic acid to a useful level, but the resulting solution had a thick, syrupy consistency which was unsuited for use in the generation of an aerosol. Similarly, efforts to solubilize all-trans retinoic acid in aqueous solution using phosphatidylcholine and phosphatidylethanolamine produced a viscous colloid which was unsuited for aerosol administration.

We next tried to use salts of the retinoids to obtain a water-soluble product for aerosol generation. When all-trans retinoic acid is treated with ammonium hydroxide, a water-soluble ammonium salt is obtained. The pH of solutions of this salt is too high (pH>10). however, for direct administration as an aerosol. Neutralization of the solution after dissolution of the retinoid led to the formation of a precipitate, both in the presence and absence of added beta cyclodextrin. Thus, the approach also failed to produce an acceptable solution for use in generating an aerosol.

Because of the solubility of all-trans retinoic acid in halogenated hydrocarbon solvents, we next considered the solubility of retinoids in various chlorofluorocarbon propellants which have been used to deliver aerosolized solutions of other pharmaceutically-active compounds. All-trans retinoic acid was found to be only slightly soluble (about 0.1 mg/ml) in 1,1,2-trichlorofluoroethane and only slightly more soluble (2 mg/ml) in 2,2-dichloro-1,1,1-trifluoroethane (HCFC-123). Thus, as an initial matter, it did not appear that these solvents would be useful for producing useful solutions of retinoids for inhalation use.

Surprisingly, however, we found that the solubility of retinoids in chlorofluorocarbon solvents could be significantly increased by the addition of alkylamines, particularly secondary, tertiary and quaternary alkylamines having alkyl groups containing from 2 to 8 carbon atoms such as trioctylamine, spermine, triethylamine or tetramethylammonium bromide, and that the resulting solutions were stable for periods of 5 days or longer, and can be solubilized by shaking. Thus, one aspect of the present invention is a solution comprising a retinoid, a chlorofluorocarbon solvent, for example HCFC-123, HCFC-134A or HCFC-227, and an alkylamine which is effective to solubilize the retinoid in the chlorofluorocarbon solvent. The solution preferably contains from 0.1 to 10 mg of the retinoid and 0.1 to 5 mg of the alkylamine, more preferably to 2 mg of the retinoid and 0.1 to 0.5 mg of the alkylamine, per ml of solution.

Retinoids useful in the present invention include the "natural retinoids" as well as pharmaceutically acceptable salts and esters thereof. Retinoids of particular interest in the present invention are all-trans retinoic acid, 13-cis retinoic acid, 9-cis retinoic acid, and salts and esters thereof.

The alkylamine is suitably a charged or uncharged secondary, tertiary or quaternary amine, having alkyl groups of 2 to 8 carbon atoms. Specific examples of suitable alkylamines include trioctylamine, triethylamine, spermine and tetrabutylammonium bromide.

This solution is packaged in an inhaler effective to provide a metered dosage of from 50 to 500 $\mu$g, preferably about 100 $\mu$g, of retinoid per inhalation as shown generally in FIG. 2. Such an inhaler is a combination of a container 1 and a dispenser assembly 2. The dispenser assembly 2 is an open tubular construction which has an actuator portion 3 for receiving the container 1, an oral tube 4 through which the retinoid is dispensed, and an actuator seat 5 which interacts with a metering valve 6 of the container 1. When the container 1 is pressed downwards within the actuator portion 3, the actuator seat 5 opens the metering valve 6, releasing a dose of retinoid 7 from the container 1, through an orifice 8 in the actuator seat 5 and out through the oral tube 4. A suitable inhaler is a Nasacort® metered dose container. Additional propellant material, for example butane, may be included within the inhaler.

The inhaler is used to administer retinoids directly to the lungs of a patient at risk of epithelial cancer of the respiratory tract. Patients in this category can be identified by behavioral characteristics. For example, individuals who are heavy smokers can be categorized as being at high-risk. Alternatively, a more quantitative approach may be used. Thus, the capacity to metabolize a small test dose of all-trans retinoic acid can be used as an indicator of risk, as described in U.S. patent application Ser. No. 07/885,130 filed May 18, 1992, which is incorporated herein by reference.

The inhaler provides dosages of from 50 to 500 $\mu$g of retinoid per inhalation and is suitably used 1 to 5 times per treatment, with the treatment being repeated 1 to 3 times per day.

A further format which can be used in accordance with the invention to administer an air-borne composition comprising a retinoid to an individual involves the use of a dry powder carrier. Suitable carriers include those which are known to be useful in dry powder inhaler compositions especially the mono-saccharides such as fructose mannitol, arabinose, xylitol and dextrose (glucose) and their monohydrates, disaccharides such as lactose maltose or sucrose and polysaccharides such as starches, dextrins or dextrans. Retinoids can be formulated into a dry powder with these carrier materials by coating the retinoid onto the surface of the carrier in a micronizer as described generally in U.S. Pat. No. 5,376,386 which is incorporated herein by reference. Dry powders containing retinoids are dispensed using known dry powder inhalers in amounts effective to provide dosages comparable to the solubilized formulations discussed above.

EXAMPLE 1

The solubility of all-trans retinoic acid in various solvents was tested as shown in Table 1. Maximum solubility was determined by weighing the residue remaining after evaporation of the solvent.

TABLE 1

| Solvent | Maximum Solubility |
|---|---|
| ethyl acetate | 10 mg/ml |
| methylene chloride | 5 mg/ml |
| HCFC-123 | ~2 mg/ml |

EXAMPLE 2

To test the ability of alkylamines to enhance the solubility of all-trans retinoic acid in chlorofluorocarbons, solutions of the retinoids in various solvents with various amounts of amine stabilizers were prepared as shown in Table 2.

TABLE 2

| Solvent | AlkylAmine - (mg/ml) | Maximum Solubility (mg/ml) |
|---|---|---|
| HCFC-123 | 0 | ~2 |
| HCFC-123 | 1.44 | ~17 |
| HCFC-123 | 7.22 | ~44 |

EXAMPLE 3

To evaluate the bioavailability of retinoids delivered by inhalation, 100 $\mu$L of an aqueous solution containing 100 $\mu$g of all-trans retinoic acid was administered via intratracheal instillation to 3 Sprague-Dawley rats, each weighing approximately 200 g. One rat was then sacrificed at three time points: 1, 6 and 24 hours after treatment. At the time of sacrifice, the chest cavity was opened, both lungs and trachea were removed en bloc, and the right and left lungs were separated by dissection. The liver was also removed, along with a sample of blood obtained by cardia puncture. The blood sample was separated by centrifugation, and plasma plus each of the aforementioned tissues were frozen for later analysis. Subsequently, the tissue was homogenized, and the homogenized tissue and plasma were extracted with ethanol. The retinoid content was assayed by HPLC, and the results shown in Table 3 were obtained.

TABLE 3

Tissue/Plasma Concentrations of Retinoic Acid After Intratracheal Instillation (ng/g or tissue or ng/ml of plasma)

| Hours | Trachea | Left Lung | Right Lung | Plasma | Liver |
|---|---|---|---|---|---|
| 1 | 2859 | 928 | 773 | 123 | 233 |
| 6 | 96 | 56 | 91 | ND | 24 |
| 24 | 30 | 22 | 21 | 178 | 23 |

The results show that this approach provides high levels of retinoid locally, but does not lead to high systemic levels.

EXAMPLE 4

Anesthetized (i.p. pentobarbitol 50 mg/kg) male Sprague-Dawley rates weighing 300 to 700 grams were treated by administration of all-trans retinoic acid by inhalation, iv injection or intratracheal injection. Inhaled and intratracheal injections were given through an endotracheal tube placed under direct vision over a guidewire as described by Weksler et al., *J. Appl. Physiol.* 76: 1823–1825 (1994). IV doeses were given by catheter injection via the right external jugular vein.

For inhalation, all-trans retinoic acid was solublized in hydrofluorocarbon 123 using tetramethylammonium hydroxide and combined with hydrofluoroalkane 134a as propellant. 21 grams of this solutions was packaged in a multdose inhaler that delivered 80 to 120 $\mu$g of all-trans retinoic acid per dose. When sprayed through the endotracheal tube, this canister supplied 49 $\mu$g/dose. However, not all of this dose was abssorbed by the rats due to escape through the nasal passages and back through the trachea. Total absorption amounted to 1–2% of the intended 250 $\mu$g dose.

For injection, an aqueous solution of all-trans retinoic acid was prepared in 20% ethanol; 10% Tween 20; 1 mM NH$_4$OH.

Animals were grouped into three experimental groups and two control groups. The control groups received no treatment or a control inhalant containing no all-trans retinoic acid. Animals in the groups receiving iv or intratracheal injections each received a single dose containing 250 $\mu$g all-trans retinoic acid. Animals in the group treated with the multidose inhaler each received three doses for a total of 147 $\mu$g of all-trans retinoic acid.

Animals were sacrificed at 5 minutes and at 1, 2, 4 and 6 hours, and blood and tissue was harvested for analysis by HPLC and histology. In addition, animals receiving the inhalant were sacrificed at 24 hours post-treatment.

Figure 3A:
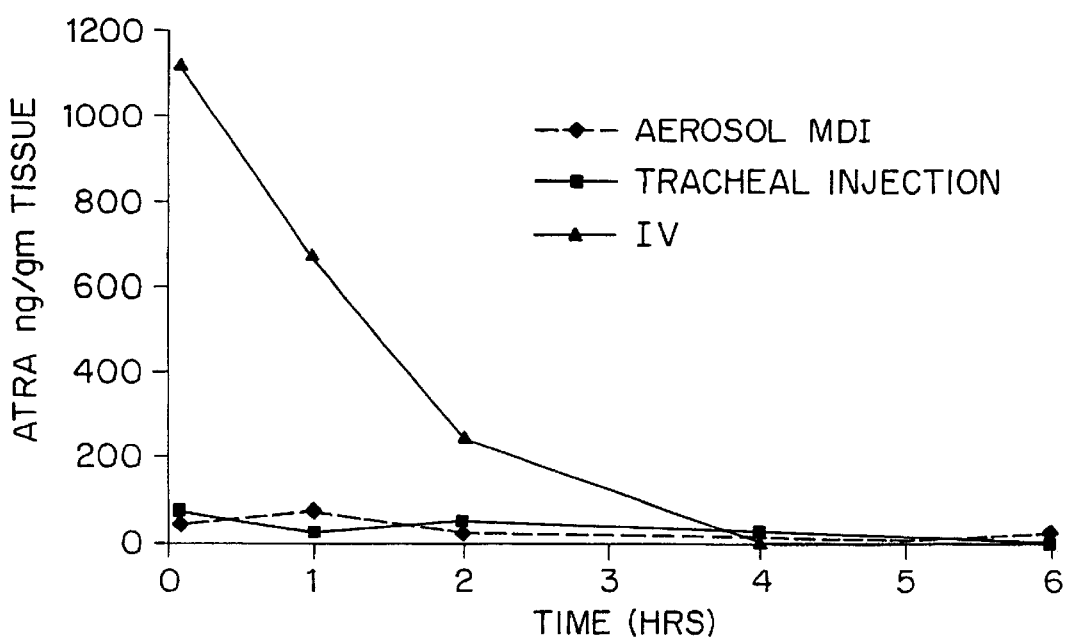
FIGS. 3A and B show plasma and liver levels of all-trans retinoic aicd after administration to rats using three different routes.
Figure 3B:
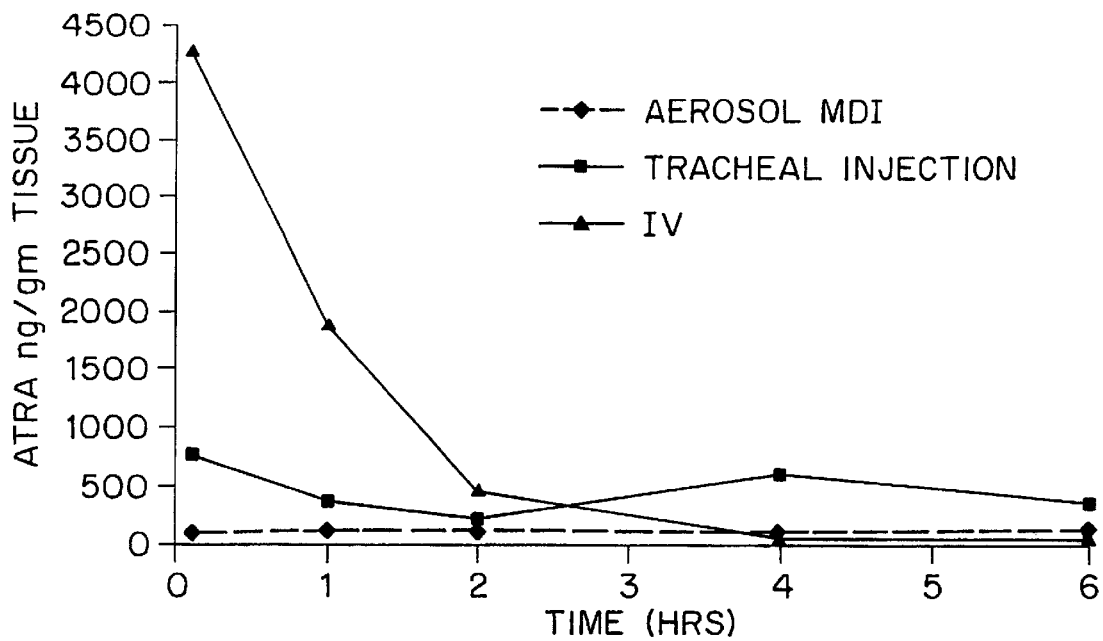
Figure 4:
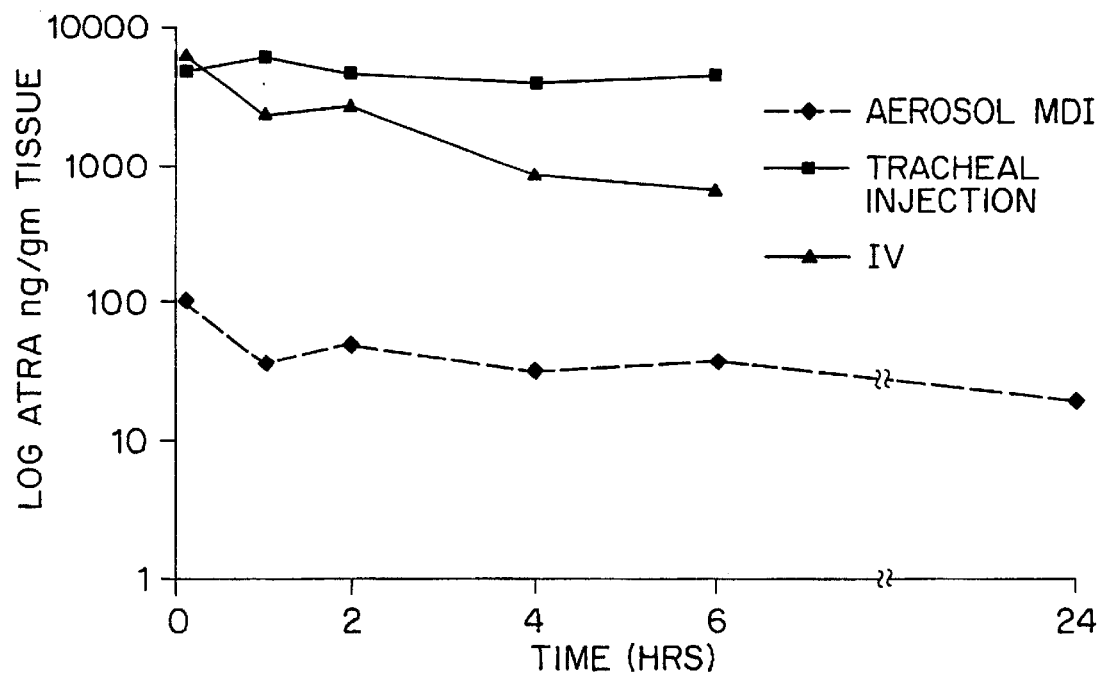
FIG. 4 shows lung tissue levels of all-trans retinoic aicd after administration to rats using three different routes.

FIGS. 3A and 3B shows the levels of all-trans retinoic acid found in the plasma and livers of animals in each of the three treatment groups. As shown, intratracheal injection and aerosol inhalation result in much lower levels of the compound in the liver. On the other hand, as shown in FIG. 4, all three treatments resulted in prolonged levels of all-trans retinoic acid in the lungs where it is desired for therapeutic efficacy. Clearance data from plasma and lung tissue is summarized in Table 4.

TABLE 4

| Administration Route | Lung t ½ (hours) | Lung AUC (ng-hr/gm) | Plasma t ½ (hours) | Plasma AUC (ng-hr/ml) |
|---|---|---|---|---|
| iv inj. | 1.9 | 11910 | 0.9 | 1385 |
| tracheal inj. | 17.7 | 26972 | 1.9 | 191 |
| aerosol inhaler | 5.4 | 262 | 3 | 171 |

As shown, the aerosol inhalation provided sustained levels of all-trans retinoic acid in the lungs with lower levels in the plasma compared to iv injections, thus offering the ability to use all-trans retinoic acid as a therapeutic agent with a reduction in systemic toxicity. Further, the tracheal injection provides a better model given the limitations of the rat as a recipient of aerosol therapy to assess the utility of such therapy in larger organism, including humans.

What is claimed is:

1. A solution comprising
   a retinoid,
   a chlorofluorocarbon solvent, and
   an alkylamine which is effective to solubilize the retinoid in the chlorofluorocarbon solvent.

2. The solution of claim 1, wherein the solution comprises from 0.1 to 5 mg of the retinoid and from 0.1 to 5 mg of the alkylamine per ml of solution.

3. The solution of claim 2, wherein the solution comprises from 1 to 2 mg of the retinoid and 0.1 to 0.5 mg of the alkylamine per ml of solution.

4. The solution of claim 1, wherein the retinoid is all-trans retinoic acid.

5. The solution of claim 1, wherein the alkylamine is a secondary, tertiary or quaternary alkylamine having alkyl groups containing from 2 to 8 carbon atoms.

6. The solution of claim 5, wherein the retinoid is all-trans retinoic acid.

7. The solution of claim 1, wherein the alkylamine is selected from the group consisting of trioctylamine, triethylamine, spermine and tetrabutylammonium bromide.

8. A method for preventing the progression of epithelial cancer of the respiratory tract in an at-risk individual, comprising administering by inhalation to the respiratory tract of the individual an air-borne composition comprising a therapeutically effective amount of at least one retinoid.

9. The method of claim 8, wherein the retinoid is administered in a solution comprising
   a retinoid,
   a chlorofluorocarbon solvent, and
   an amine which is effective to solubilize the retinoid in the chlorofluorocarbon solvent.

10. The method of claim 9, wherein the solution comprises from 0.1 to 10 mg of the retinoid and from 0.1 to 5 mg of the alkylamine per ml of solution.

11. The method of claim 10, wherein the solution comprises from 0.1 to 2 mg of the retinoid and 0.1 to 0.5 mg of the alkylamine per ml of solution.

12. The method of claim 9, wherein the alkylamine is a secondary, tertiary or quaternary alkylamine having alkyl groups containing from 2 to 8 carbon atoms.

13. The method of claim 12, wherein the retinoid is all-trans retinoic acid.

14. The method of claim 9, wherein the alkylamine is selected from the group consisting of trioctylamine, triethylamine, spermine and tetrabutylammonium bromide.

15. The method of claim 1 wherein the retinoid is all-trans retinoic acid.

16. An inhaler comprising
- (a) a body member containing a reservoir for pharmaceutically-active substance;
- (b) a composition disposed within the reservoir, said composition comprising at least one retinoid and a carrier suitable for dispensing from the inhaler; and
- (c) means for dispensing a metered dose of the composition from the inhaler.

17. The inhaler of claim 16, wherein the composition is a solution comprising a retinoid, a chlorofluorocarbon solvent, and an alkylamine which is effective to solubilize the retinoid in the chlorofluorocarbon solvent.

18. The inhaler of claim 17, wherein the comprises from 0.1 to 10 mg of the retinoid and from 0.1 to 0.5 mg of the alkylamine per ml of solution.

19. The inhaler of claim 18, wherein the solution comprises from 1 to 2 mg of the retinoid and 0.1 to 0.5 mg of the alkylamine per ml of solution.

20. The inhaler of claim 17, wherein the retinoid is all-trans retinoic acid.

21. The inhaler of claim 17, wherein the alkylamine is a secondary, tertiary or quaternary alkylamine having alkyl groups containing from 2 to 8 carbon atoms.

22. The inhaler of claim 21, wherein the retinoid is all-trans retinoic acid.

* * * * *